(12) United States Patent
Marotta

(10) Patent No.: US 7,281,927 B2
(45) Date of Patent: *Oct. 16, 2007

(54) STABLE DENTAL ANALOG

(76) Inventor: Leonard Marotta, 222 W. Islip Rd., West Islip, NY (US) 11795

( * ) Notice: Subject to any disclaimer, the term of this patent is extended or adjusted under 35 U.S.C. 154(b) by 0 days.

This patent is subject to a terminal disclaimer.

(21) Appl. No.: 11/449,461

(22) Filed: Jun. 8, 2006

(65) Prior Publication Data

US 2006/0228674 A1   Oct. 12, 2006

Related U.S. Application Data

(63) Continuation of application No. 10/056,101, filed on Jan. 24, 2002, now Pat. No. 7,059,856.

(60) Provisional application No. 60/316,832, filed on Aug. 31, 2001.

(51) Int. Cl.
*A61C 9/00* (2006.01)

(52) U.S. Cl. .................................................. 433/213

(58) Field of Classification Search ................ 433/173, 433/213, 214, 225
See application file for complete search history.

(56) References Cited

U.S. PATENT DOCUMENTS

| | | | |
|---|---|---|---|
| 2,745,180 A * | 5/1956 | Kiernan, Jr. ................. | 433/175 |
| 2,857,670 A * | 10/1958 | Kiernan, Jr. ................. | 433/175 |
| 3,981,079 A * | 9/1976 | Lenczycki ................... | 433/174 |
| 4,331,423 A | 5/1982 | Yanney, Jr. | |
| 4,955,811 A | 9/1990 | Lazzara et al. | |
| 5,013,242 A * | 5/1991 | Prezmecky ................. | 433/174 |
| 5,125,841 A | 6/1992 | Carlsson | |
| 5,542,847 A * | 8/1996 | Margulies ................... | 433/173 |
| 5,658,147 A | 8/1997 | Phimmasone | |
| 5,762,500 A | 6/1998 | Lazarof | |
| 5,766,009 A | 6/1998 | Jeffcoat | |
| 5,829,981 A | 11/1998 | Ziegler | |
| 5,904,483 A | 5/1999 | Wade | |
| 5,934,906 A | 8/1999 | Phimmasone | |
| 6,039,568 A * | 3/2000 | Hinds ........................ | 433/175 |
| 6,068,478 A | 5/2000 | Grande et al. | |
| 6,213,773 B1 | 4/2001 | Gittleman | |
| 6,332,777 B1 | 12/2001 | Sutter | |
| 6,508,650 B2 | 1/2003 | Gittleman | |
| 6,799,970 B2 * | 10/2004 | Martin et al. ................ | 433/173 |
| 7,059,856 B2 * | 6/2006 | Marotta ....................... | 433/214 |

FOREIGN PATENT DOCUMENTS

WO    WO98/52490    11/1998

\* cited by examiner

*Primary Examiner*—Ralph A. Lewis
(74) *Attorney, Agent, or Firm*—Alfred M. Walker; Frank Tolin; Mark Bender

(57) ABSTRACT

An implant analog includes an abutment that can be mounted in the dental lab replica of the relevant section of a patient's mouth more securely than heretofore possible. Because of the implant analog, a crown will attach more accurately to the implant in the patient's mouth. The analogs have a pin or other protrusion that projects from the base of the analog. The analog has substantially the same height and dimensions as a conventional implant and abutment.

8 Claims, 5 Drawing Sheets

STABLE DENTAL ANALOG

RELATED APPLICATIONS

This application is a continuation of application Ser. No. 10/056,101, filed Jan. 24, 2002 now U.S. Pat. No. 7,059,856 and claims priority under 35 U.S.C. 120 therefrom, which application claims benefit under 35 U.S.C. 119 (e) of provisional application Ser. No. 60/316,832 filed Aug. 31, 2001.

FIELD OF THE INVENTION

This invention relates generally to the construction of a dental prosthesis that is attached to an implant in the bone of a person's jaw.

BACKGROUND OF THE INVENTION

Dental implants are a common treatment for the replacement of a missing tooth or missing teeth. An implant is placed into the bone in a person's jaw in a variety of fashions and using a variety of systems. The bone and the implant adhere together in a process known as osseointegration, thus enabling a person to have a new tooth or set of teeth held into position in the jaw utilizing screws to hold them down.

Many firms manufacture complete systems of dental implants and prosthetic components for subsequent attachment to the implant. In a typical construction, the implant has an axially threaded hole at its top, that is, the proximal end, near the gum surface. After the implant has integrated with the bone, the gum of the implant is opened to expose the tapped hole. Then a transmucosal abutment is attached to the tapped hole of the implant and extends to a level above the gum or substantially to the gum surface. The protruding free end of the abutment is constructed for attachment of a prosthesis. For preventing rotation of the prosthesis, the protruding end of the abutment requires a non-round shape and a hexagon protrusion has been widely used. A recessed hexagon is also popular with some systems. The abutment also includes a central threaded hole concentric with the threaded hole of the implant and extending inward toward the jaw bone.

A false tooth or frame is provided with a hole therethrough, known in the industry as a chimney, and a non-round recess in its base corresponds in shape to the protruding non-round cross section for the abutment. Thereby, the crown can be connected to the abutment and relative rotation between them is prevented so long as critical contours of the abutment and the recess in the crown are maintained.

To prevent the crown or bridge from lifting axially from the abutment, a final screw is passed into the chimney opening and engages the tapped hole in the implant by way of the abutment so as to hold the crown axially to the abutment and to the implant. Thus, the crown cannot rotate about the abutment or implant because it is mated with the special contours on the exposed end of the abutment. The abutment is similarly mated to the proximal or outer end of the implant. The crown cannot pull away from the abutment when the screw has been tightened into place.

Finally, the chimney above the screw is filled with a composite material that hardens and is shaped as part of the crown to look lie a natural tooth.

There are many variations in construction.

In an alternative method, the crown is attached directly to a non-round protrusion of the implant and is held directly to the implant by a gold screw without use of an intermediate abutment.

The implant is intended to be a permanent fixture in the jaw bone. The abutment and crown may be replaced if necessary due to damage or poor fit by gaining access to the screw head by way of the chimney, and backing off the screw so that the crown and abutment or crown to the implant can be separated from the implant. Thus repairs may be made of an abutment and crown with no or little inconvenience.

Therefore, the fit of an implant with the crown or frame must be perfect. If a prosthesis is placed into the mouth and does not seat correctly, the implant or abutment can be damaged. If an implant is damaged there are not many options for its repair. In cases where there have been a poor fit, the screws have broken inside the abutment requiring the replacement of the abutment. There have been cases where the screw broke inside the implant. The implants cannot be replaced without surgically removing them. Placing a new implant in the same spot is not an advised option.

Among related patents disclosing dental analogs include U.S. Pat. No. 6,142,782 of Lazarof, which shows a dental analog with annular wings. However, the annular wings do not hinder rotating and therefore misplacement of the analog within the replica cast stone. The annular wings of Lazarof do not intersect with the cast stone material enough to prevent rotation.

OBJECTS OF THE INVENTION

Accordingly, it is the object of the invention to provide a method for insuring the most accurate seating possible of a prosthesis to an abutment or implant.

SUMMARY OF THE INVENTIONS

The present invention comprises an implant analog that may include a standard abutment that can be mounted in the dental lab replica of the relevant section of a patient's mouth more securely than heretofore possible. Because of the inventive implant analog, dental labs can now create a crown that will attach more accurately to the implant in the patient's mouth. The analogs of the present invention are desirably longer than the analogs used heretofore and have a pin that projects from the base of the analog. Desirably, the inventive analogs have a side ridge. Moreover, the analog has substantially the same height and dimensions as a conventional implant and abutment. In a preferred embodiment, the analog of the present invention is formed from stainless steel.

A careful confidential experiment was conducted at New York University of School of Dental Medicine by Dr. C. Jager, Dr. G. R. Goldstein, Dr. E. Hittelman and the Applicant herein. The experiment was designed to compare the performance of a prior art analog of NOBEL BIOCARE®, as shown in FIG. 9, to that of one embodiment of the present invention, as shown in FIG. 4. A statistically significant improvement for the present invention was found in terms of framework fit. Also, resistance to applied torque was found to be significantly improved for the analog of this invention.

The experiment evaluated torque prostheses to laboratory dental implant analogs. The study evaluated the movement of the prior art analog of NOBEL BIOCARE®, as shown in FIG. 9, and the embodiment shown in FIG. 4 of the present invention. Both were torqued to 20 Ncm in a reinforced type IV die stone. 80 analogs were divided into groups of 4 analogs, including three of the prior art analog shown in FIG. 9 with one of the present invention shown in FIG. 4. These analogs were embedded in thirty equal blocks of Type IV plaster stone using a prefabricated four unit implant framework. Of the twenty analogs, ten were imbedded in the stone at a depth of four cm and ten were imbedded at a depth of six cm from the implant platform. These groups of ten were then divided into groups of five each, where five of the prior art analogs shown of the present invention in FIG. 9 were torqued to 20 Ncm in each group and five analogs shown in FIG. 4 were torqued to 20 Ncm. The initial framework was used to evaluate the fit of each analog therein. In the 4 mm depth group of the prior art shown in FIG. 9, two of the five samples (40%) did not allow the framework to fit the analog. In the 6 mm depth of the prior art analogs shown in FIG. 9, three of the five samples (60%) did not allow the framework to fit. However, all of the dental analogs shown in FIG. 4 of the present invention fit back to the cast.

As a result, the analogs of the present invention, as shown in FIG. 4, were able to resist movement within a stone cast when torqued, unlike a significant portion of the prior art dental analogs shown in FIG. 9.

Therefore, the dental analogs of the present invention have unexpected, beneficial results not achievable with the dental analogs of the prior art shown in FIG. 9.

DETAILED DESCRIPTION OF THE INVENTION

Simplified, the construction of the prosthesis begins after the osseointegration of the implant with the dentist making an impression of the relevant section of the patient's mouth. When constructing the prosthesis, the dentist makes an impression including an impression coping. Desirably, the impression material employed is hard and elastic when set, such as the materials sold under the trade names IMPRAGUM, EXPRESS and PRESIDENT.

Once the impression material hardens, the tray containing the impression is sent to a dental lab where the prosthesis is made. The dental lab uses this impression to make a replica of the relevant section of the patient's mouth. Typically, the replica is made of gypsum, and is made to reproduce the milieu into which the prosthesis is to fit, including, for example, any hexagonal protrusion or recession in the abutment the dentist is using.

Figure 1:
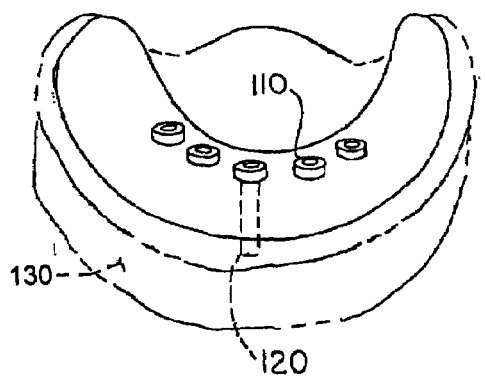
FIG. 1 is a view of a dental lab replica showing the position of an analog and an abutment.

For example, FIG. 1 shows a view of dental lab replica 130 with analog 120 and abutment 110.

Figure 2:
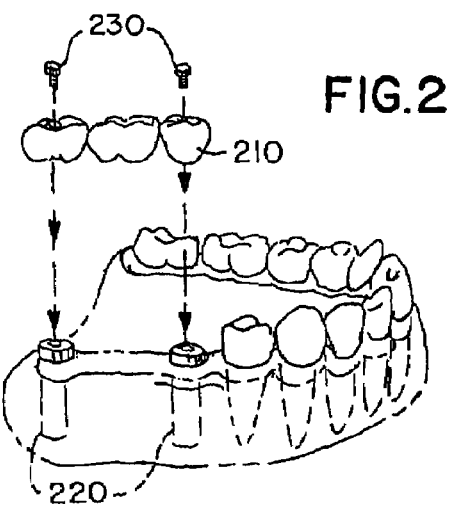
FIG. 2 is a view of a lower jaw about to receive a prosthesis and having two implants.

Moreover, FIG. 2 shows an actual patient lower jaw with two implants 220, a three tooth prosthesis 210 and screws 230 to retain prosthesis 210 in implants 220.

In making the impression, the impression coping is attached to the implant in the same way the final prosthesis will attach. The impression coping rests flush on top of the implant, or implant and abutment, with a guide screw passing through and into the implant. The impression coping remains in the impression in the same position that was in the mouth and the guide screw must be removed before the impression can be removed from the patient's mouth.

In making the dental lab jaw model, or replica, the analog is attached to the impression coping with a guide screw going through the impression coping and into the analog. All of the teeth in the relevant portion of the mouth are replicated in the model, which desirably is made of gypsum. The goal is to have the analog in the replica in the position that corresponds to the position of the implant in the patient's mouth, including the orientation of any protrusion or recess.

The present day tools offered by the implant manufacturers utilize brass or stainless steel analog.

The configuration of the prior art analogs replicates the internal thread dimension of the implant or abutment and copies the shape of the external or internal hexagon. However, the outside diameter of a prior art analog maintains a shape that is not consistent with the needs of the dentist or technician in constructing the prosthesis. Conventional analogs are too small and are removed from the gypsum model too easily. Moreover, the exterior surface of conventional analogs are too smooth which permits the analog, and thus the prosthesis, to rotate in the model during construction of the prosthesis. Such rotation moves the hexagonal position of the prosthesis into a position that does not match the corresponding position of the implant in the patient's mouth.

Figure 3:
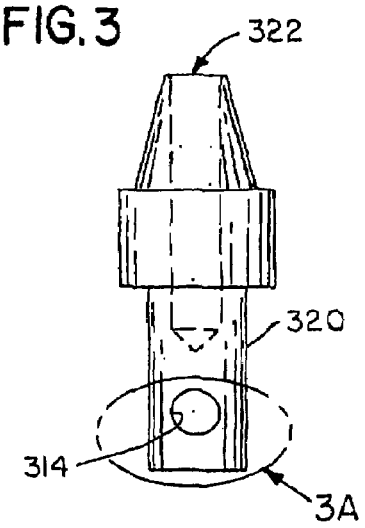
FIG. 3 is a view of an embodiment of the present invention incorporating a conical abutment.

In contrast to the prior art conventional, easily rotatable and dislodgable dental analogs, the present invention is a new analog that will not allow any rotation in the gypsum model. In a preferred embodiment, as shown in FIGS. 3 and 3A, the analog 320 of the present invention is substantially longer and has a unique feature of a transverse pin 312 or other protruding geometric shaped member extending through hole 314 in its side.

Figure 3A:
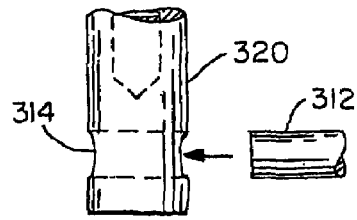
FIG. 3A is a partial view taken within the phantom circle of FIG. 3, shown rotated ninety degrees for clarity.
Figure 4:
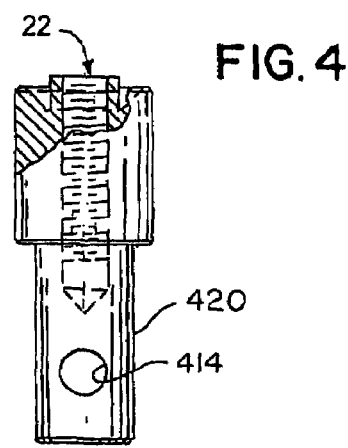
FIG. 4 is a view of an embodiment of the present invention incorporating a standard abutment.

FIG. 4 shows analog 420 with abutment 22 and hole 414 for insertion of a pin therein, similar to pin 312 of FIG. 3A.

Figure 5:
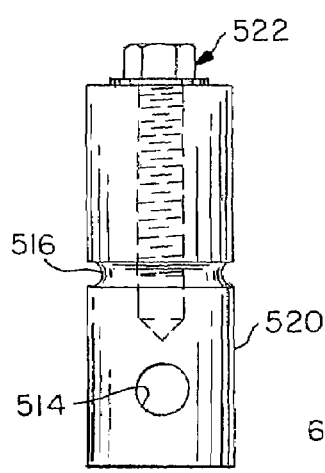
FIG. 5 is a view of an embodiment of the present invention corresponding to an implant with a hexagonal protrusion.
Figure 6:
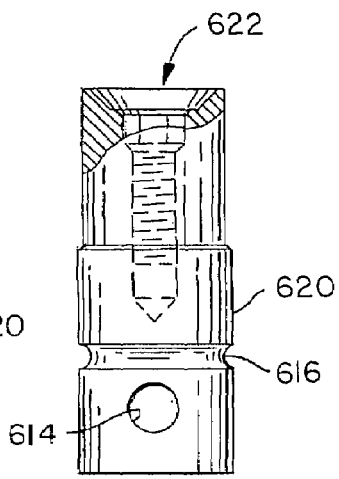
FIG. 6 is a view of an embodiment of the present invention corresponding to a large diameter implant with a hexagonal recess.
Figure 7:
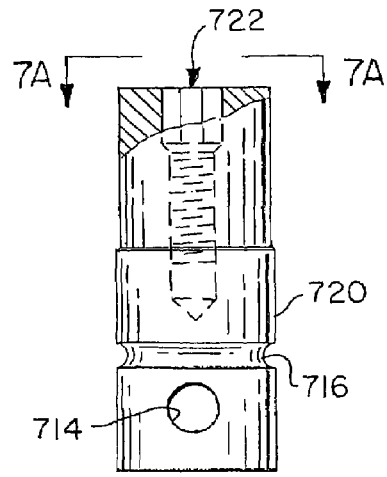
FIG. 7 is a side elevation view in partial cross section of an embodiment of the present invention corresponding to an implant with a hexagonal recess.
Figure 7A:
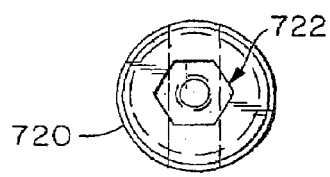
FIG. 7A is a top plan view thereof.

As shown in FIGS. 5, 6, and 7, these dental analogs 520, 620 and 720 of the present invention are preferably ridged with annular recesses, these dental analogs 520, 620 and 720 on their respective sides to gain better retention inside the gypsum model.

Analogs 420, 520, 620 and 720 have respective pins (not shown) similar to transverse pin 312 of analog 320 of FIG. 3A. These pins 312 are located at the base of the respective analogs 320, 420, 520, 620 and 720 to lock the position. These transverse pins 312 prevent horizontal, vertical or cylindrical movement of the analogs 320, 420, 520, 620, and 720 within the model.

Figure 28:
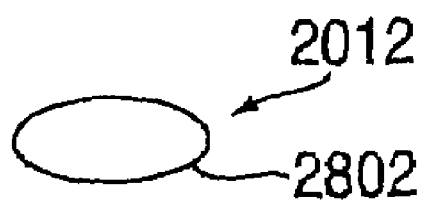
FIG. 28 depicts a cross-sectional view of a protrusion in an analog having a substantially oval shape 2802.
Figure 29:
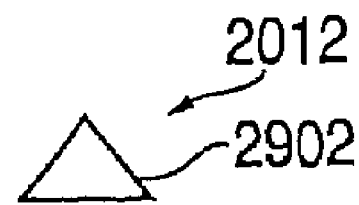
FIG. 29 depicts a cross-sectional view of a protrusion in an analog having a substantially triangular shape.
Figure 30:
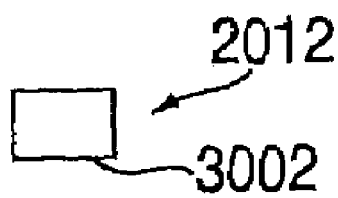
FIG. 30 depicts a cross-sectional view of a protrusion in an analog having a substantially square shape.
Figure 31:
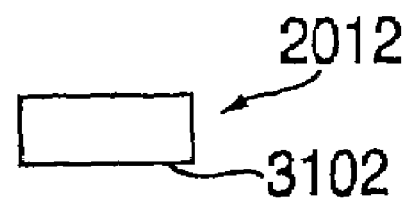
FIG. 31 depicts a cross-sectional view of a protrusion in an analog having a substantially rectangular shape; and, FIG. 32 depicts a cross-sectional view of a protrusion in an analog having a substantially hexagonal shape 3202.
Figure 32:
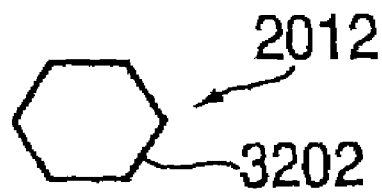

Conventional implants have a standardized system of heights, measurements and dimension for implants and abutments. The respective inventive analogs 320, 420, 520, 620, 720 of the present invention can have a shape which incorporates a conical abutment 322 (FIGS. 3 and 3A), a standard abutment 422 (FIG. 4), a hexagonal protrusion 522 (FIG. 5), a large hexagonal recess 622 (FIG. 6) or a hexagonal recess 722 (FIG. 7), as these terms are used in the dental industry. For example, FIGS. 28-32 depict cross-sectional views of protrusion embodiments having various shapes. Illustratively, FIGS. 28-32 are described with respect to protrusion 2012 however that description is not intended in any way to limit the scope of the invention. For example, it is appreciated that extensions 2051 may in various other embodiments have the shapes depicted in FIGS. 28-32. FIG. 28 depicts a cross-sectional view of protrusion 2012 having a substantially oval shape 2802. FIG. 29 depicts a cross-sectional view of protrusion 2012 having a substantially triangular shape 2902. FIG. 30 depicts a cross-sectional view of protrusion 2012 having a substantially square shape 3002. FIG. 31 depicts a cross-sectional view of protrusion 2012 having a substantially rectangular shape 3102. FIG. 32 depicts a cross-sectional view of protrusion 2012 having a substantially hexagonal shape 3202.

Analogs 520, 620 and 720 also bear annular grooves 516, 616 and 716.

The analogs 320, 420, 520, 620 and 720 of the present invention are machined to specified mechanical tolerances. In particular, the internal thread of the inventive analogs are closer to the threads of actual implants and abutment. This closer approximation to the actual implants insures that the guide screw goes into the implant the same number of turns the guide screw goes into the analog, and maintains the prosthesis in the same position relative to the patient's mouth as the prosthesis had with respect to the replica. The internal or external hexagon is also closer in dimensions to the actual implant. As a result, the prosthesis will fit on the analog and on the actual implant or abutment in the manner intended.

Another complication in the construction of dental analogs is that it is often necessary to construct a large frame using soldered connections. The present methods of soldering require a duplicate model of high heat tolerance gypsum investment be made with the present day analogs. The frame is soldered on that model. The success rate of these solder connections is far lower than expected in the industry. The present invention allows a more accurate solder connection. The present invention also holds better in the invested model and keeps the analogs from moving in the model.

EXAMPLE

Figure 8:
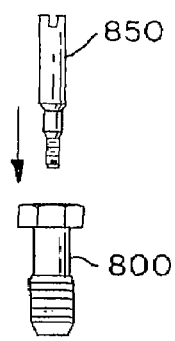
FIG. 8 shows a conventional impression coping with depth indications from 2-5 mm.

In the single tooth prosthetic work, the impression is taken from the fixture level. As shown in FIG. 8, one type of conventional impression coping 800 has an internal hexagon at the base, which corresponds to the hexagon of the abutment. The coping has depth indications for assessment of proper abutment size, 2 mm, 3 mm, 4 mm, and 5 mm. The upper margin of the abutment-like part indicates 6 mm. The impression coping is typically made of titanium.

The impression coping is used together with a special guide pin (e.g., a DCA 098), 850, for a single tooth (the guide pin used to secure the prosthesis to the implant typically has a different thread).

Typically, in the laboratory, any undercuts of the impression coping are blocked out before pouring the impression (including the depth indications). This blocking is especially important when the longest abutment is used. This precaution prevents fracturing the cast when separating the model and the impression coping.

Figure 9:
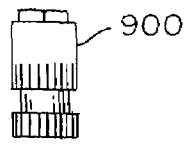
FIG. 9 shows a conventional prior art fixture replica, or analog, which is replaced by analog according to the present invention.
Figure 10:
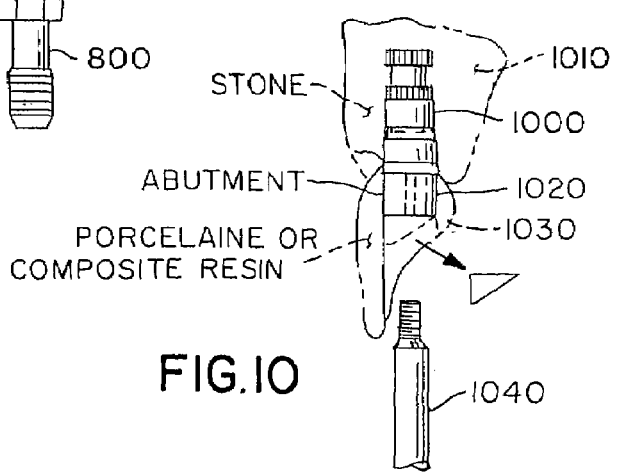
FIG. 10 shows the placement of a fixture replica, either a conventional or according to the present invention, in the lab replica that is to be secured to an abutment and a crown via a guide pin.

During the Laboratory procedure, an analog, for example a conventional prior art analog 900 shown in FIG. 9, or an analog of the present invention such as the analogs of FIGS. 3-7, is used in the laboratory jaw model, or replica, to represent the implant in the working cast. This is illustrated in FIG. 10 where analog 1000 is set in the laboratory jaw model, or replica, 1010, and the abutment 1020 and crown 1030 are secured to the jaw model by guide pin 1040. The analog has the same top hexagon and internal thread as the implant. In contrast to the stainless steel analogs of the present invention, conventionally, analogs were typically made of nickel-plated brass.

Figure 11:
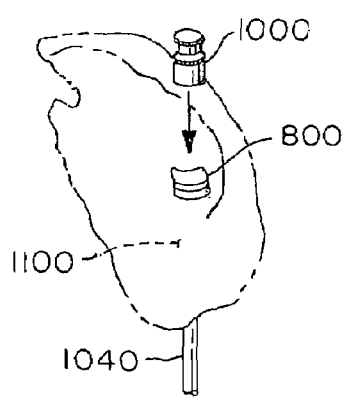
FIG. 11 shows the attachment of a fixture replica, either a conventional or according to the present invention, to an impression coping that is fixed in an impression of the relevant section of a patient's mouth prior to the casting of the lab replica.

FIG. 11 shows an impression 1100 containing an impression coping 800 being attached to an analog 1000 via guide pin 1040. Once the analog 1000 is secured to the impression coping 800 by the guide pin 1040, the impression 1100 is used to cast he laboratory jaw model, or replica, from stone, such as gypsum.

Figure 12:
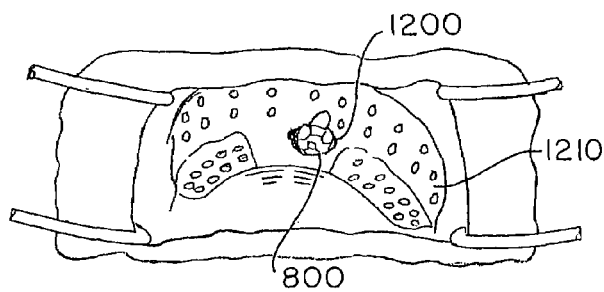
FIG. 12 shows a dental impression tray modified to provide access to the impression coping that is secured to the implant in a patient's mouth by a guide pin.
Figure 15:
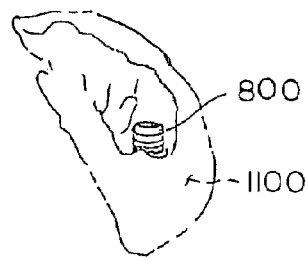
FIG. 15 shows the impression containing the impression coping.

The impression 1100 containing the impression coping 800 can be prepared in any conventional manner. For example, as shown in FIG. 12, one can make a hole 1200 in an acrylic-resin stock tray 1210 for access to the impression coping 800 which is secured to the implant by the guide screw.

Figure 13:
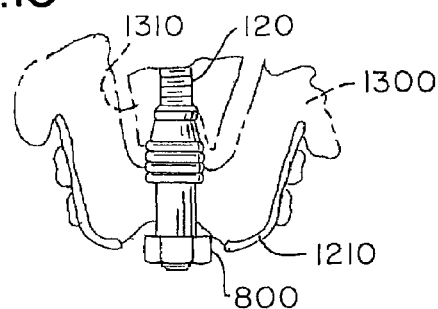
FIG. 13 shows the excess material around the impression coping in a tray containing impression material, the impression coping being secured to the implant in the patient's mouth by a guide pin.

FIG. 13 shows tray 1210 loaded with an impression material of choice 1300 in the mouth with impression coping 800 secured to implant 120 within the patient's jaw 1310.

FIG. 13 also shows the removal of any excess material around impression coping 800 once impression material 1300 has set.

Impression coping 800 is then secured to tray 1210 with auto-polymerizing acrylic resin 1400. The orientation of the hexagonal head of the implant 120 should be maintained when the impression 1100 is removed. Next, guide pin 850 is unscrewed and impression 1100 is carefully removed form the patient's mouth.

As noted before, FIGS. 3-7 show different embodiments of the dental analogs 320, 420, 520, 620 and 720 of the present invention each using a transverse rod pin 312 or tube within hole 314, 414, 514, 614, or 714, in the base section of each analog 320, 420, 520, 620, or 720 to enhance the anchoring of the analog in the plaster of the replica. Each of the different embodiments uses a different style of abutment 322, 422, 522, 622, or 722 to match that which the dentist had used in the patient's actual implant.

For example, FIG. 3 shows a conical abutment 322 for analog rod 320 and FIG. 4 shows a standard recessed abutment 422 for analog rod 420. FIG. 5 shows an abutment 522 with a hexagonal protrusion for analog rod 520, FIG. 6 shows a large diameter abutment 622 with a hexagonal recess, for analog rod 620, and FIG. 7 shows an abutment 722 with a hexagonal recess for analog rod 720.

Figure 16:
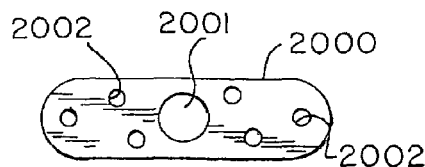
FIG. 16 is a top view of an engagement plate of this invention which is used to provide improved anchorage for a conventional analog.
Figure 14:
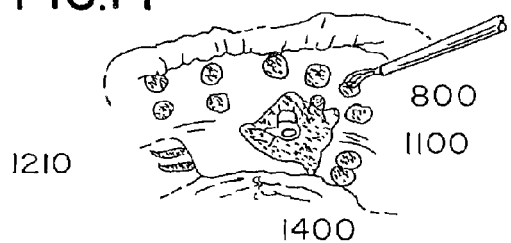
FIG. 14 shows a means of securing the impression coping to the tray containing the impression material with an acrylic resin.

FIG. 16 shows another embodiment of this invention in the form of a flat engagement plate 2000 which is used to provide enhanced anchoring of a standard prior art analog 900 (see FIG. 9) in the replica plaster.

Figure 17:
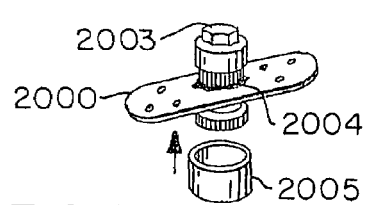
FIG. 17 is an exploded side view of the engagement plate of FIG. 16 attached to a conventional analog.

As shown in FIG. 17, the conventional analog 2003 is inserted through central hole 2001 and adhesively bonded 2004 at an oblique angle. Perforations 2002 enhance adhesion to immobilize plate 2000 in replica plaster. An optional hollow sleeve 2005 can be used to extend the vertical height of analog 2003, to further promote its anchoring within the replica plaster.

Figure 18:
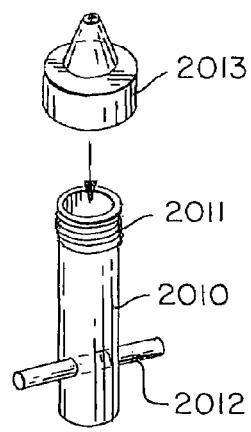
FIG. 18 is a perspective view of an analog body with a transverse tube configured to screw into a variety of abutments.
Figure 19:
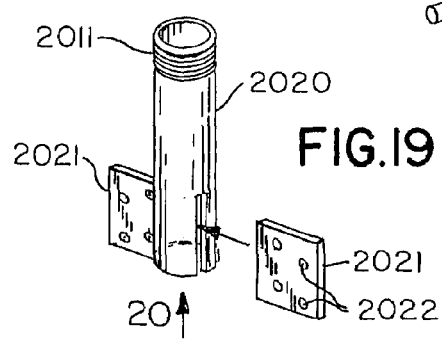
FIG. 19 is a perspective view of an analog body with transverse wings.
Figure 21:
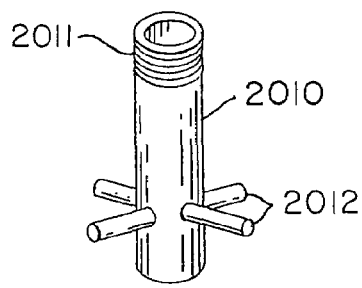
FIG. 21 is a perspective view of an analog body with coplanar transverse tubes at right angles.
Figure 23:
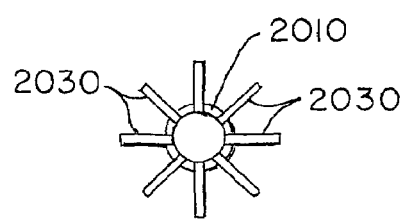
FIG. 23 is a bottom view of an analog body with eight co-planar transverse tube segments.
Figure 25:
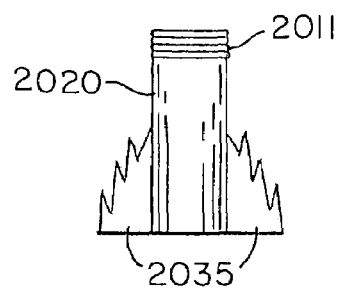
FIG. 25 is a side elevation of an analog body with serrated side extensions.
Figure 26:
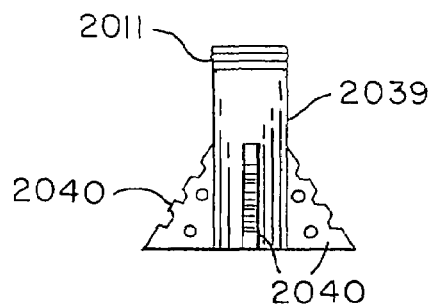
FIG. 26 is a side elevation of an analog body with four serrated and perforated side extensions.
Figure 27:
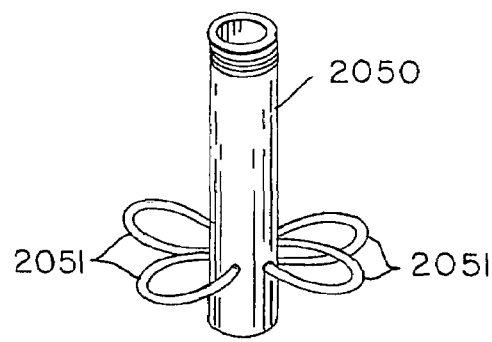
FIG. 27 is a perspective view of an analog body with looped side extensions.

It is further noted that optional removable hollow sleeve 2005 can also have any of the protrusions shown in the other drawing figures, such as protrusion rods 2012 of FIG. 18 or FIG. 21, protrusion 2022 of FIG. 19, protrusion wings 2030 of FIG. 23, protrusion barbs 2032, protrusion wings 2035 of FIG. 25, protrusion wings 2040 of FIG. 26 or protruding loops 2051 of FIG. 27.

FIG. 18 shows the concept for a series of additional embodiments of analogs of this invention which use a tubular body 2010 with external threads 2011 at the top end. These threads screw into mating female threads on a series of abutments 2013 (here illustrated as a conical abutment) which are supplied to match the style and size actually implanted in the patient's jaw.

Figure 20:
FIG. 20 is a bottom view of an analog body with transverse wings.

Therefore, analogs of this general category of embodiments can be matched with a variety of abutments 322, 422, 522, 622, or 722 (as described in FIGS. 3-7). The analog 2010 with conical abutment 2013 of FIG. 18, similar to analog 320 with a conical abutment 322, uses a transverse tube or rod 2012 to aid in anchoring body 2010 in plaster. Slotted body 2020 as shown in FIG. 19 accepts two rectangular wings 2021 (as shown in bottom view of FIG. 20) with perforations 2022 as yet another embodiment to resist rotation within, and extraction from, the replica plaster.

The embodiment shown in FIG. 21 uses coplanar radial transverse tubes 2012 at right angles to each other to provide anchorage.

Figure 22:
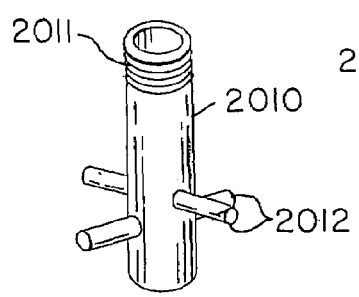
FIG. 22 is a perspective view of an analog body with non-coplanar oblique tubes.

The embodiment shown in FIG. 22 uses two oblique tubes 2012 which penetrate body 2010 as anchorage.

The bottom view of the embodiment of FIG. 23 shows eight equally spaced tubular segments 2030 attached to body 2010 to provide anchorage in replica plaster.

Figure 24:
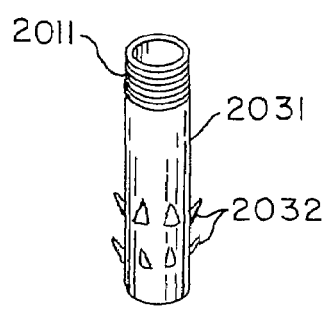
FIG. 24 is a perspective view of an analog body with angled spikes.

FIG. 24 shows an embodiment of an analog using tubular body 2031 with upward angled spikes 2032 in two rows to provide anchorage.

The embodiment of FIG. 25 shows slotted body 2020 with a pair of serrated triangular wings 2035 to provide anchorage in the replica plaster.

FIG. 26 shows an embodiment of an analog with body 2039 with four slots accommodating four perforated and serrated triangular wings 2040 to rigidly anchor it to the plaster of a replica.

Furthermore, FIG. 27 shows an embodiment of an analog using tubular body 2050 with one or more outwardly extending looped extensions 2051 to promote anchorage.

It is further know that other modifications may be made to the present invention without departing from the scope of the invention, as noted in the appended Claims.

I claim:

1. A method of preparing dental crowns efficiently and accurately, comprising the steps of
   a. preparing an analog dental crown mounting post which is a replica of an upper portion of a mounting post already or to be mounted in a mouth of a user, said analog dental crown mounting post having a downwardly extending elongated member with at least one removable and insertable radially extending anchoring extension within a bore disposed near a bottom end of said elongated member, said at least one extension passing completely through said elongated member;
   b. inserting bottom-end-down said elongated member into a dental crown casting mold;
   c. securing said elongated member temporarily in place within said casting mold;
   d. adding settable plaster molding material to said casting mold so as to embed said bottom end of said elongated member with said at least one extension by surrounding said bottom end of said elongated member with said plaster molding material;
   e. allowing said plaster molding material to set and harden with said elongated member and extensions embedded within said molding material; and
   f. utilizing said analog dental crown firmly anchored and secured to make a dental crown.

2. The method of claim 1 wherein said at least one extension comprises at least one pair of anchoring projections oppositely and radially extending from a bottom end of said elongated member.

3. The method of claim 2 wherein said extensions comprise at least two pairs of anchoring projections oppositely and radially extending from a bottom end of said elongated member and wherein said at least two pairs of said projections are spaced apart longitudinally on said elongated member near said bottom end thereof.

4. The method of claim 3 wherein said at least one pair of opposing radially extending anchoring projections comprises rigid rods.

5. A method of preparing dental crowns efficiently and accurately, comprising the steps of
   a. preparing an analog dental crown mounting post which is a replica of an upper portion of a mounting post already or to be mounted in a mouth of a user, said analog dental crown mounting post having a downwardly extending elongated member with at least one radially extending anchoring extension disposed near a bottom end of said elongated member, said at least one extension extending outward from said elongated member;
   b. inserting bottom-end-down said elongated member into a dental crown casting mold;
   c. securing said elongated member temporarily in place within said casting mold;
   d. adding settable plaster molding material to said casting mold so as to embed said bottom end of said elongated member with extensions by surrounding said bottom end of said elongated member with said plaster molding material;
   e. allowing said plaster molding material to set and harden with said elongated member and extensions embedded within said molding material; and
   f. utilizing said analog dental crown firmly anchored and secured to make a dental crown.

6. The method of claim 5 wherein said at least one extension comprise at least one pair of anchoring projections oppositely and radially extending from a bottom end of said elongated member.

7. The method of claim 6 wherein said extensions comprise at least two pairs of anchoring projections oppositely and radially extending from a bottom end of said elongated member and wherein said at least two pairs of said projections are spaced apart longitudinally on said elongated member near said bottom end thereof.

8. The method of claim 7 wherein said at least one pair of opposing radially extending anchoring projections comprises rigid rods.

* * * * *